(12) United States Patent
Hatch

(10) Patent No.: US 8,845,589 B2
(45) Date of Patent: Sep. 30, 2014

(54) DEVICE AND METHODS FOR DELIVERING FLUIDS TO ANIMALS

(76) Inventor: Thomas Clyde Hatch, Lexington, KY (US)

( * ) Notice: Subject to any disclaimer, the term of this patent is extended or adjusted under 35 U.S.C. 154(b) by 960 days.

(21) Appl. No.: 12/802,234

(22) Filed: Jun. 1, 2010

(65) Prior Publication Data

US 2010/0292658 A1 Nov. 18, 2010

Related U.S. Application Data

(63) Continuation-in-part of application No. 12/009,419, filed on Jan. 18, 2008, now abandoned.

(51) Int. Cl.
| | |
|---|---|
| *A61M 5/00* | (2006.01) |
| *A61M 31/00* | (2006.01) |
| *A61M 25/00* | (2006.01) |
| *A61D 7/00* | (2006.01) |
| *A61D 1/14* | (2006.01) |
| *A61M 25/06* | (2006.01) |

(52) U.S. Cl.
CPC ............... *A61M 31/00* (2013.01); *A61M 25/00* (2013.01); *A61D 7/00* (2013.01); *A61D 1/14* (2013.01); *A61M 2025/0681* (2013.01)
USPC .......................................... 604/171

(58) Field of Classification Search
USPC ................... 604/14, 41, 516, 174, 95.01, 171
See application file for complete search history.

(56) References Cited

U.S. PATENT DOCUMENTS

| | | | | |
|---|---|---|---|---|
| 3,681,504 | A | * | 8/1972 | Johnston et al. ............... 514/632 |
| 4,050,460 | A | * | 9/1977 | Magrath ........................ 604/516 |
| 4,413,986 | A | * | 11/1983 | Jacobs ............................ 604/14 |
| 4,923,440 | A | * | 5/1990 | Genaro ............................ 604/14 |
| 4,938,746 | A | * | 7/1990 | Etheredge et al. ............. 604/265 |
| 5,926,015 | A | * | 7/1999 | Pharr ............................. 324/114 |
| 6,039,714 | A | * | 3/2000 | Cracauer et al. .............. 604/174 |
| 6,213,960 | B1 | * | 4/2001 | Sherman et al. ................. 601/41 |
| 6,527,748 | B1 | * | 3/2003 | Suzuki ........................... 604/171 |
| 6,554,793 | B1 | * | 4/2003 | Pauker et al. ................. 604/95.01 |

* cited by examiner

*Primary Examiner* — Manuel Mendez

(57) ABSTRACT

Embodiments of the present invention feature devices and methods for providing fluids to or venting gas from animals which feature a tube and a sheath in which the sheath covers the tube as the tube in inserted into the oral cavity and esophagus.

28 Claims, 9 Drawing Sheets

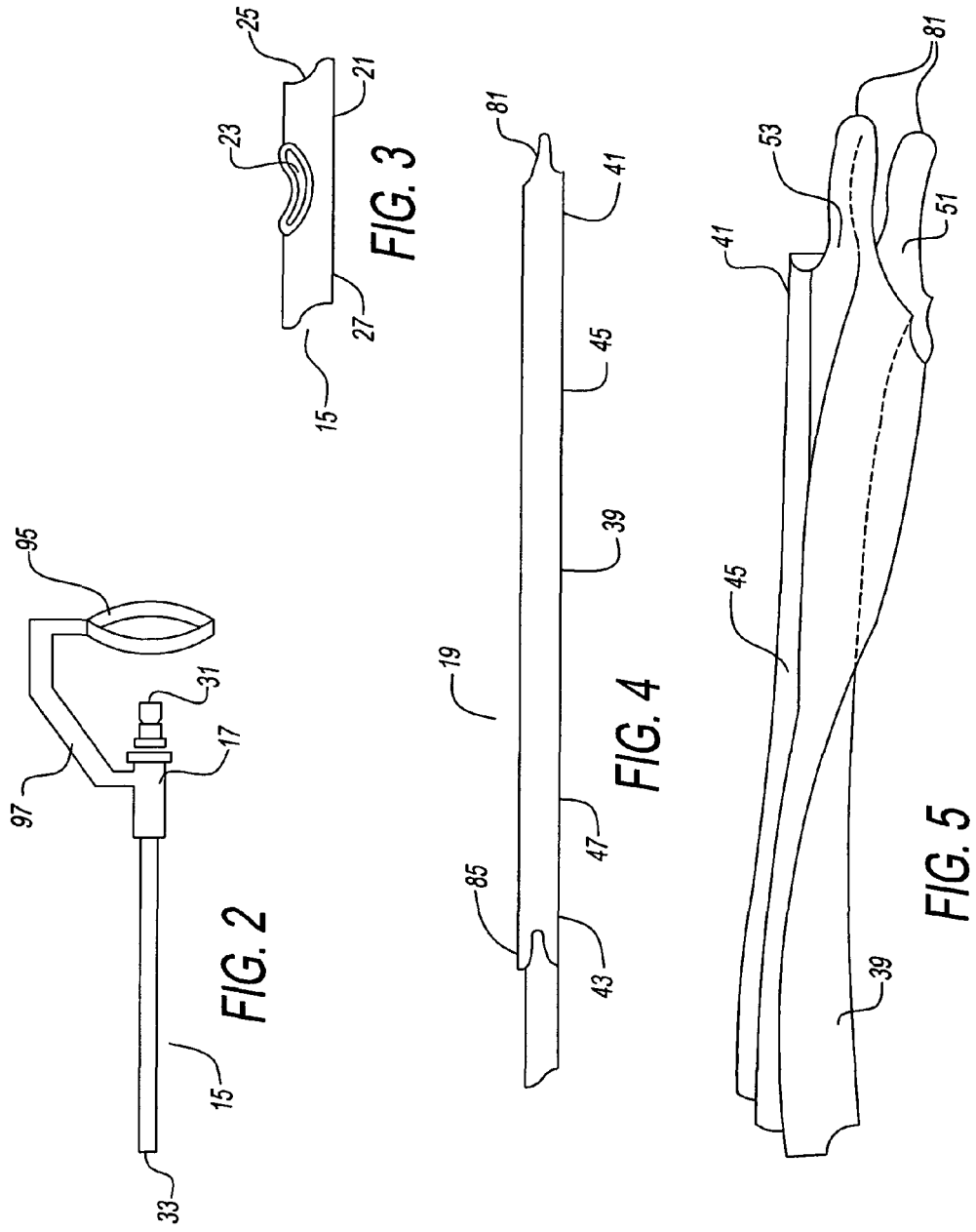

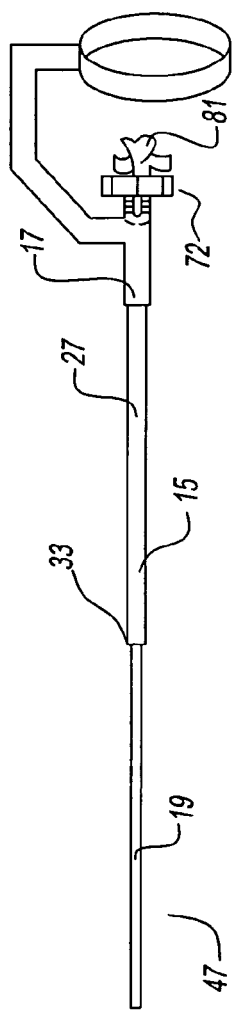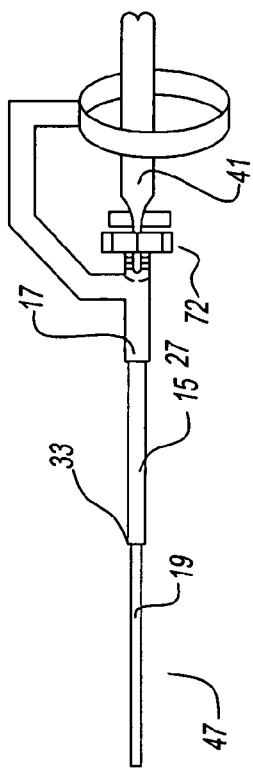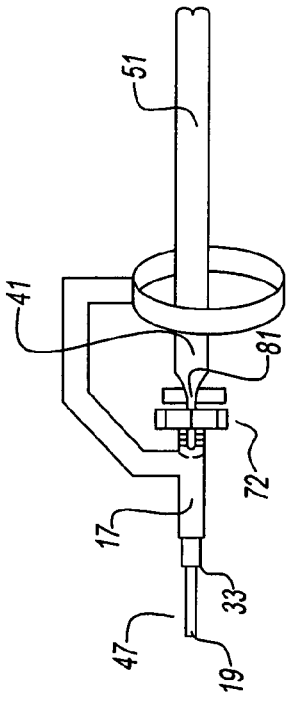

DEVICE AND METHODS FOR DELIVERING FLUIDS TO ANIMALS

CROSS-REFERENCE TO RELATED APPLICATIONS

This application is a continuation in part of U.S. Ser. No. 12/009,419 filed Jan. 18, 2008 now abandoned, the entire contents of which are incorporated herein by reference.

STATEMENT REGARDING FEDERAL SPONSORSHIP

The present invention was not made or developed with Federal sponsorship.

FIELD OF INVENTION

This application is directed to devices and methods for delivering fluids to animals, and, in particular, for applications in animal husbandry.

BACKGROUND OF THE INVENTION

A newborn animal, such as a calf, needs to ingest colostrum immediately after birth to obtain the maternal antibodies that will protect it from disease. However, on modern dairy farms, calves are often removed from their dams before nursing, requiring that colostrum be administered to the calf through artificial means, either a nipple and bottle or a stomach tube. The use of a stomach tube to administer the colostrum or other fluids saves the dairy farmer a significant amount of time. While a calf can nurse through an artificial nipple, this may require an inordinate amount of time when the nursing reflex is weak. A weak nursing reflex is common in newborn animals. And, there is uncertainty as to whether the fluids will and are delivered unless the dairy farmer watches each calf.

Young animals also suffer from a high rate of diarrhea, or scours. Scours can be caused by administering too much liquid feed to the animal or by infectious disease pathogens such as *E. coli* or rotavirus. In either case, the dehydration that occurs as a sequela to scours must be reversed to return the young animal to health. In many instances, fluid therapy with electrolytes must be continued for several days to prevent mortality.

Occasionally, young animals experience milk bloat. This can occur when milk enters the rumen, rather than the abomasum, and ferments, forming copious quantities of gas. When the gas cannot escape, the pressure can build up and cause death. A properly placed stomach tube can vent such gases and keep an animal from dying.

Though placing a stomach tube in an animal can serve several important purposes, there are obvious drawbacks to the procedure. These drawbacks apply to the insertion of any device into a body cavity. For example, it is imperative that multi-use prior art devices be disinfected between uses to prevent horizontal transmission of diseases across animals. And, it is difficult to maintain sterility in any farm environment, particularly where livestock are being kept.

Most instructions on how to use stomach tubes state that the tube should be dipped in a fluid to lubricate the outer surface to make it easier to insert into the esophagus. This is an especially important issue in the case of a dehydrated neonate with scours whose mucosal surfaces lining the throat may already be semi-dry. A stomach tube must be inserted gently.

There exists a need for devices and methods for delivering fluids to animals with a minimum of trauma and while maintaining contact surfaces sterile even though the area in which the fluids are administered are not.

SUMMARY OF THE INVENTION

Embodiments of the present invention are directed to devices and methods for delivering fluids to animals. One embodiment of the present invention is directed to a device for administering a fluid to an animal, wherein the animal has at least an oral cavity, esophagus and stomach. The fluid is administered through a tube and the tube has at least one tube wall having an interior tube surface defining a tube passage and at least one exterior tube surface. The at least one tube wall has a tube length to distend from the oral cavity into the esophagus. The exterior tube surface has a diameter not greater than the diameter of the animal's esophagus. The at least one tube wall defines a first tube end and a second tube end. The first tube end is for placing in the oral cavity and into the esophagus; with the second tube end extending out of the oral cavity for administering fluids. One device comprises a sheath having a first sheath end, a second sheath end, a first sheath section and a second sheath section. The first sheath end is at one terminus and a second sheath end at a second terminus. The sheath is sized and shaped to have the first sheath section towards the first sheath end and the second sheath section toward the second sheath end. The sheath has at least one first sheath wall having a length greater than the length of the tube such that upon being extended the sheath forms a cylinder-like form. The at least one sheath wall is flexible and has at least one first sheath surface and at least one second sheath surface. The sheath has a first position in which the first sheath surface of the first sheath section is positioned facing itself and the second sheath surface is facing away from itself and a second position in which the second sheath surface of the first sheath section faces itself and the first sheath surface faces away from itself. The sheath moves from the first position to the second position upon inserting the sheath through tube and folding the first sheath section at the first tube end to invert the first sheath section and drawing the second sheath section of said sheath into the tube passageway, forming a fluid conduit for dispensing fluids with the first sheath section of the sheath shielding the exterior surface of the tube from contact with the oral cavity or esophagus of the animal.

Thus, the sheath is placed in the esophagus, assuming the second position as the tube is compelled further, such that the animal does not experience trauma from the abrasion on the tube or the sheath itself. No tube or sheath surface ever slides along a mucosal surface. Once positioned, the sheath receives fluids or vents air and can be withdrawn from the esophagus without the animal ever experiencing direct contact with the tube and without any portion of the sheath placed in direct contact with the oral cavity compelled lower in the digestive system. The sheath and the tube are preferably withdrawn from the esophagus and oral cavity in the reverse of the manner in which the sheath and tube are originally inserted. That is, the sheath is withdrawn into the first tube end as the tube is withdrawn from the esophagus and oral cavity.

Another aspect of the invention is a pre-formed sheath having one or more chemicals coated on the first sheath surface. Upon insertion of the sheath into the oral cavity and esophagus of an animal, the chemicals on the first sheath surface of the first sheath section contact the mucosal surface of the animal, triggering closure of the esophageal groove. A preferred medicament is selected from the group comprising guanidine, sodium chloride, copper sulfate and sodium bicarbonate solutions.

Preferably, the first sheath end has rabbit ear-type tab elements constructed and arranged to fold over the tube exterior wall as the first sheath section is in a position inside the tube. A preferred tab element projects from the first sheath end. and has gripping surfaces, such as, by way of example, without limitation, knurling, holes, slots, adhesives, buttons and the like, to allow a user to grasp the sheath as said tube is pushed into the esophagus of an animal. Preferably, the tab element cooperates with a nut that presses against threads and a stationary ring on the guide collar, thereby holding the tab element in a stationary position. The guide collar is positioned around the tube in sliding engagement therewith and the tab element affixed to or held to the guide collar by a cooperating attachment means. The tube is compelled through the guide collar as the tube assumes a position in the animal's oral cavity and esophagus. A preferred guide collar and tab element cooperate to releaseably engage.

A preferred guide collar is attached to a head halter. The halter engages the head of an animal, aligns the guide collar with the oral cavity and prevents the guide collar and the end of the insertion sheath from contacting the oral cavity. A preferred head halter has an alignment arm affixed to the guide collar. The alignment arm extends to the head halter which encircles or engages the head of the animal as the arm hold the guide collar in front of the mouth of the animal in stationary position.

A preferred tab element cooperates with a loading rod. The loading rod has a rod end with rod attachment means to releaseably engages the tab element. The loading rod is attached to the sheath by said tab element and the rod is passed through the tube to load the sheath in place. The tab element is released from the rod attachment means and placed on the ring. Alternatively, an insertion sheath can be folded in an accordion-like fashion to reduce the width of the lay-flat sheath from approximately 1⅜ inch to ⅜ inch.

Preferably, the second sheath section is placed in communication with a fluid supply where fluids are to be administered to the animal, or, the device further comprises a fluid supply. A preferred device has a sheath which has a third section integral with the second section. The first section and the second section have a volume per unit of length and said third section has a volume per unit of length in which said third section has a volume per unit of length greater than said first section and said second section. That is, the third section expands or is capable of expanding to allow said third section to hold a greater quantity of fluid per unit length than said first section and said second section. Preferably, the sheath has a supply seal interposed between the third and second sections which seal can be broken to release fluid from the third section into the second section to be administered to the animal. In the alternative, the device comprises a supply clamp to allow the third section to hold fluid prior to release to the second section.

Preferably, the sheath has a fourth section in communication and integral with the third section. The fourth section has a volume per unit length approximately that of or smaller than said first section and said second section; that is, the fourth section is the same or narrower. The fourth section has the second end of the sheath for filling the sheath and storing fluid in the third section. The fourth section is used for closing the sheath. Preferably, the fourth section has a length which is sufficient to form a simple knot. Other closing means comprise clamps, zip seals, and folds.

Preferably, the fluid for the third section is selected from the group consisting of colostrum, milk, electrolyte solution, oral drugs, vitamins, anti-bloat compounds, amino acids, mineral oil, dissolved or suspended therapeutic powders and granules and nutrients.

The first two sections of the sheath are at least twice the length of the esophageal tube being inserted into the esophagus. A preferred sheath is comprised of one or more materials selected from the group consisting of metals, polyfoils, or plastic.

A preferred sheath is packaged or bundled with other sheaths for ready use. For example, without limitation, a first sheath is joined to at least one second sheath held by a tear line. Or, a plurality of sheaths are held on a roll or bunched and/or folded into a box or bag or other dispensing package. A preferred sheath held in packaging or on a roll presents tab elements to the user to withdraw the sheath.

A preferred device is combined with a tube, previously described. The tube is comprised of one or more materials selected from the group consisting of metals, plastics and rubber. A preferred tube has an everting ball surface at its terminus. The everting ball is a smooth surface substantially free of sharp angles which may catch the sheath.

The device may further comprise a guide collar as described above. Preferred guide collars further comprise a head halter.

Those skilled in the art will readily recognize that the sheath, tube and guide collar can be bundled as a kit. Those skilled in the art will readily recognize that the sheath, constructed and arranged to operate with a tube and guide collar, is of the nature of a disposable item which can be discarded after a single use. The tube and guide collar can be used repeatedly with new sheaths.

A further embodiment of the present invention is directed to a method of administering a fluid to or venting gas from an animal. The method comprises the step of administering fluid or venting gas through a tube. The tube has at least one tube wall having an interior tube surface defining a tube passageway and at least one exterior tube surface. The at least one tube wall has a tube length to distend from the oral cavity into the esophagus. The exterior tube surface has a diameter not greater than the diameter of the animal's esophagus. The at least one tube wall defines a first tube end and a second tube end. The first tube end is for placing in the oral cavity and into the esophagus; with the second tube end extending out of the oral cavity for administering fluids. The method further comprises the step of fitting a device to the tube. The device comprises a sheath having a first sheath end, a second sheath end, a first sheath section and a second sheath section. The first sheath end is at one terminus and a second sheath end at a second terminus. The sheath is sized and shaped to have the first sheath section towards the first sheath end and the second sheath section toward the second sheath end. The sheath has at least one first sheath wall having a length greater than the length of the tube such that upon being extended the sheath forms a cylinder. The first sheath wall is flexible and has at least one first sheath surface and at least one second sheath surface. The sheath has a first position in which the first sheath surface of the first sheath section is positioned facing itself and the second sheath surface is facing away from itself and a second position in which the second sheath surface of the first sheath section faces itself and the first sheath surface faces away from itself. The method further comprises the step of moving the sheath from the first position to the second position upon pulling the sheath through a tube and folding the first sheath section at the first tube end to invert the first sheath section and drawing the second sheath section of said sheath into the tube passageway, forming a fluid conduit for dispensing fluids with the first sheath section of the sheath shielding the exterior surface of the tube from contact with the oral cavity or esophagus of the animal.

The step of moving the sheath from the first position to the second position is preferably performed as the tube is moved through the oral cavity of an animal and into the esophagus.

These and other features and advantages will be apparent to those skilled in the art upon viewing the drawings and reading the detailed description that follows.

BRIEF DESCRIPTION OF THE DRAWINGS

FIG. 2 is a perspective view of the semi-flexible esophageal tube located within a guide collar that is connected to the head halter.

FIG. 3 is a partial cross sectional view of the semi-flexible esophageal tube

FIG. 4 is a perspective view of an insertion sheath with rabbit ear tab means and a portion of a second insertion sheath that has not yet been folded into an accordion-type longitudinal fold.

FIG. 5 is a perspective view of the insertion sheath unfolded at the rabbit ear tab element portion.

FIG. 14A is a perspective side view of the insertion sheath attached to guide collar tab attachment means representing a starting position before insertion into the oral cavity of an animal.

FIG. 14B is a perspective side view of the insertion sheath after it has been partially inverted by the esophageal tube.

FIG. 14C is a perspective side view of the insertion sheath after it has been fully inverted by the esophageal tube.

DETAILED DESCRIPTION OF THE INVENTION

Preferred embodiments of the present invention will now be described in detail as devices and methods for delivering fluids to animals. However, embodiments of the present invention can be used for venting rumen or stomach gases, placing solids in the stomach or removing fluids.

Figure 1:
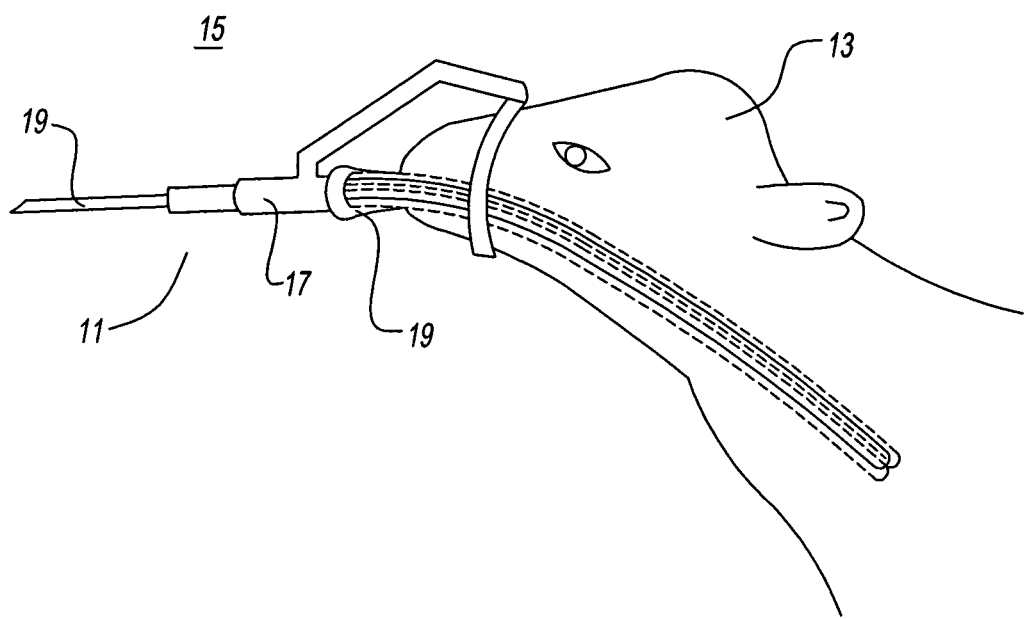
FIG. 1 is a partial cross-sectional side view of the insertion sheath in the oral cavity and esophagus of a calf after it has been inverted by the esophageal tube.

FIG. 1 provides an overview of the present invention in which a device, generally designated by the numeral 11, is shown in partial cross section in place in an animal 13 for delivering fluid. The device 11 is comprised of the following major elements: an esophageal tube 15, a guide collar 17, and insertion sheath 19.

FIG. 2 provides a perspective view of the esophageal tube 15, the guide collar 17, the head halter 95 and arm 97 that connects the guide collar 17 to the head halter 95. The esophageal tube 15 has a first tube end 31 and a second tube end 33. The first tube end 31 is for placing in the oral cavity and into the esophagus; with the second tube end 33 extending out of the oral cavity for administering fluids and for manipulation by a operator.

Focusing briefly on the partial cutaway view in FIG. 3, the esophageal tube 15 has at least one tube wall 21 having an interior tube surface 23 defining a tube passage 25 and at least one exterior tube surface 27. The at least one tube wall 21 has a tube length to distend from the oral cavity into the esophagus. The exterior tube surface 27 has a diameter not greater than the diameter of the animal's esophagus.

Esophageal tube 15 is comprised of one or more materials selected from the group consisting of metals, plastics and rubber.

FIG. 4 is a perspective view of two insertion sheaths 19 connected serially. Multiple sheaths 19 can be connected in this fashion, with a tearable boundary 85 between sheaths 19. Insertion sheath 19 has at least one insertion sheath wall 39. Sheath 19 has a first sheath end 41, a second sheath end 43, a first sheath section 45 and a second sheath section 47. The first sheath end 41 is at one terminus and a second sheath end 43 at a second terminus. A preferred insertion sheath 19 is comprised of one or more materials selected from the group consisting of metals, polyfoils, or plastic.

Sheath 19 is packaged or bundled with other sheaths 19 for ready use. The plurality of sheaths may be held on a roll, bunched and/or folded into a box or other dispensing package. The plurality of insertion sheaths are used with esophageal tube 15 and guide collar 17 with which the sheaths may be bundled or can be considered a disposable item and acquired separate and apart from esophageal tube 15 and guide collar 17.

Insertion sheath 19 is sized and shaped to have the first sheath section 45 towards the first sheath end 41 and the second sheath section 47 toward the second sheath end 43. Upon being extended the insertion sheath 19 forms a cylinder-like form. As used herein, the term cylinder-like form refers to a conventional cylinder and also multisided forms which can function as a fluid conduit. The at least one first sheath wall 39 has a length that is at least twice the length of the esophageal tube 15 such that the sheath 19 can be everted to cover the interior tube surface 23 and exterior tube surface 27.

Turning now to FIG. 5 in particular, the insertion sheath wall 39 is flexible and has at least one first sheath surface 51 and at least one second sheath surface 53. The insertion sheath 19 has a first position in which the first sheath surface 51 of the first sheath section 45 is positioned facing itself and the second sheath surface 53 is facing away from itself; and, a second position in which the second sheath surface 53 of the first sheath section 45 faces itself and the first sheath surface 51 faces away from itself.

Figure 6:
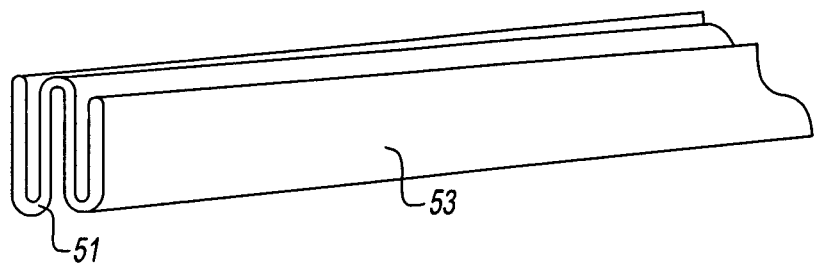
FIG. 6 is an enlarged perspective view of the insertion sheath folded along it longitudinal axis.

FIG. 6 illustrates how insertion sheath 19 can be folded in an accordion-like fold to reduce its width from approximately 1⅜ inches down to ⅜ inch or less, which width can be passed through the tube passageway 25 of esophageal tube 15.

Figure 7:
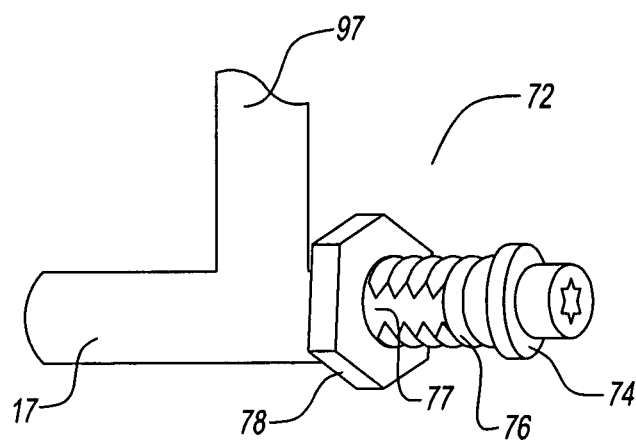
FIG. 7 is a perspective view of the guide collar and nut that can be tightened against a stationary ring.

FIG. 7 is a partial perspective view of guide collar 17 and arm 97 which connects the guide collar 17 to the head halter 95. Guide collar 17 has a tab attachment means 72. The preferred tab attachment means 72 consists of a ring 74 that is a larger diameter than the insertion sheath 19, a partially threaded shaft 76, a cut-out of the threaded shaft 77 and a nut 78.

Figure 8:
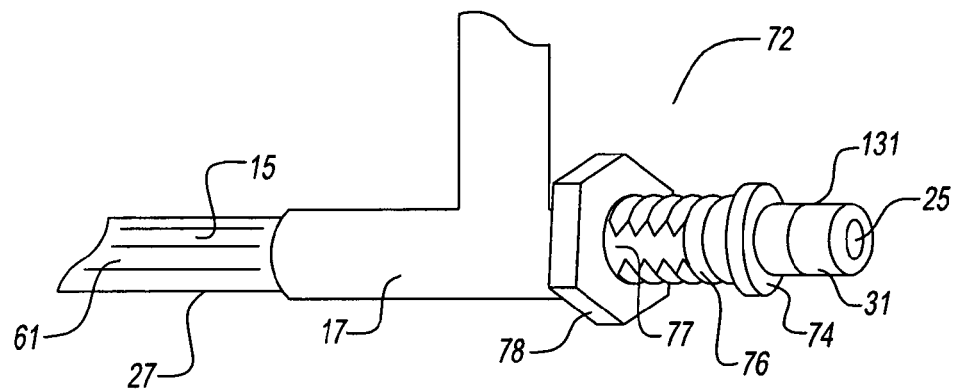
FIG. 8 is a perspective view of the esophageal tube situated within the guide collar.

FIG. 8 is a partial perspective view of the guide collar 17, the attachment means 72 and the esophageal tube 15. At the first tube end 31 is an inverting ball 131 circumscribing tube passageway 25. Esophageal tube 15 has raised ridges 61 located on the exterior tube surface 27. The raised ridges 61 serve to keep the insertion tube 15 oriented in guide collar 17 and to reduce the total friction surface between the second sheath surface 53 of the first sheath section 45 and the raised ridges 61 as the esophageal tube 15 moves insertion sheath 19 from position one to position two.

Figure 9:
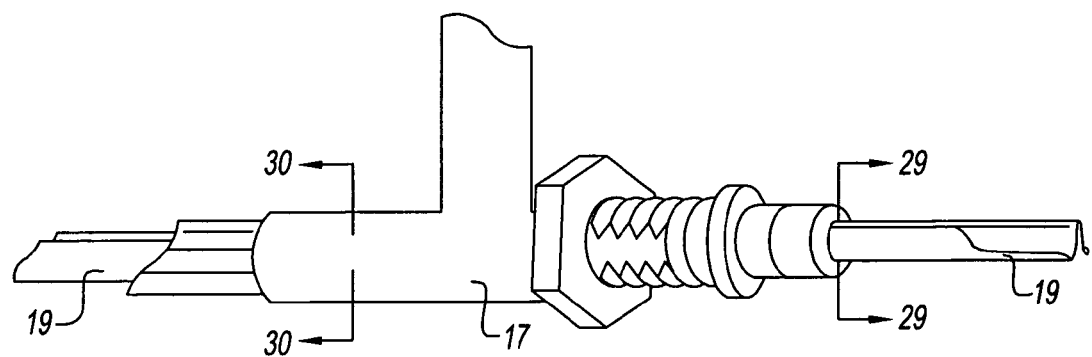
FIG. 9 is a perspective view of the folded insertion sheath situated within the esophageal tube which is situated within the guide collar.

FIG. 9 is a partial perspective view of insertion sheath 19 placed in passageway 25 of esophageal tube 15 which is situated in guide collar 17.

Figure 10:
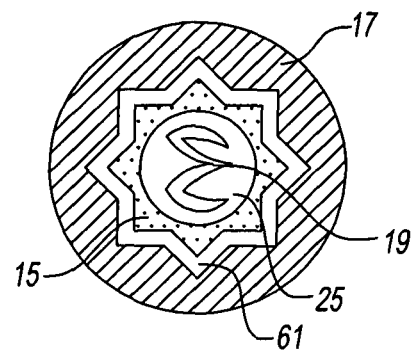
FIG. 10 is a cross sectional end view of the insertion sheath situated in the esophageal tube situated within the guide collar taken along line 30_30 of FIG. 9.

FIG. 10 is a cross-sectional end view taken at line 30_30 of FIG. 9, with folded insertion sheath 19 situated in tube passageway 25 inside esophageal tube 15, with raised ridges 61, all situated in guide collar 17.

Figure 11:
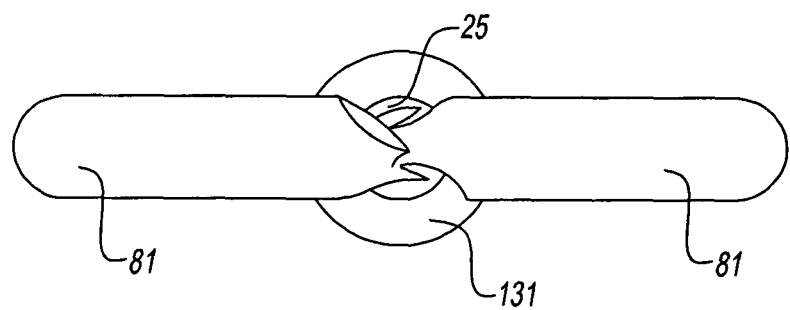
FIG. 11 is an end view along line 29_29 of FIG. 9 of the rabbit ear tabs of the insertion sheath as they extend out from the everting ball on the end of the esophageal tube.

FIG. 11 is an end view taken at line 29_29 of FIG. 9 showing insertion sheath 19 with tab elements 81 projecting out of tube passageway 25 and extending out from everting ball 131.

Figure 12:
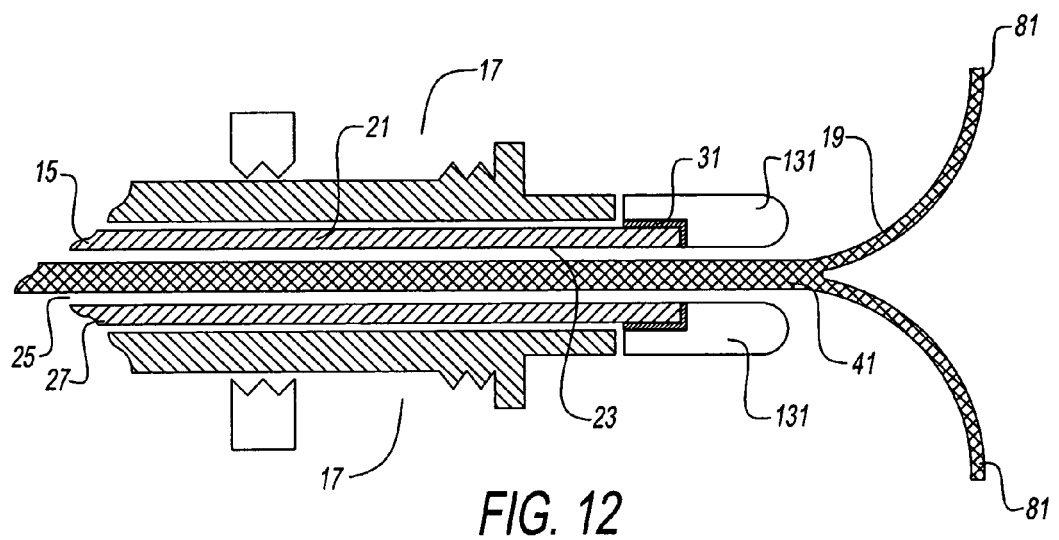
FIG. 12 is a cross sectional top view of the insertion sheath situated within the esophageal tube which is situated within the guide collar.

FIG. 12 is a cross-sectional top view of insertion sheath 19 with tab elements 81 attached at first sheath end 41 extending from passageway 25 through everting ball 131, which is situated on the first tube end 31 of esophageal tube 15, which in turn is situated inside guide collar 17.

Figure 13:
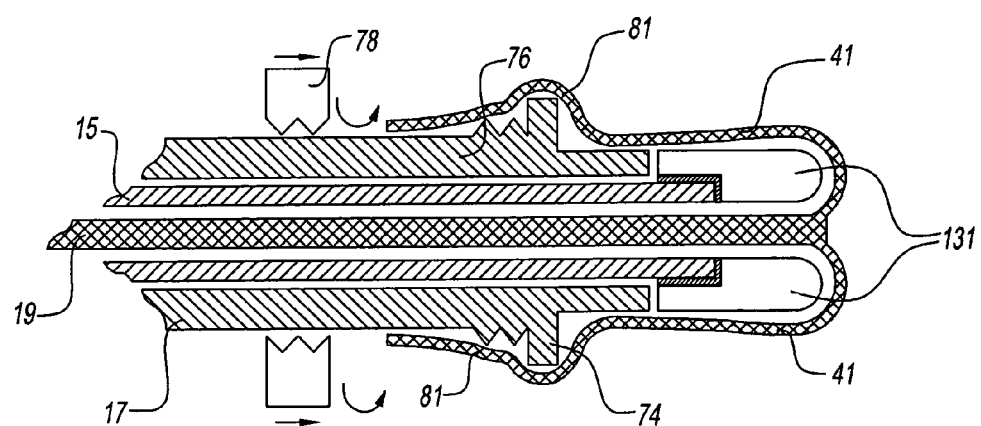
FIG. 13 is a cross-sectional top view of the rabbit ear tab elements of the insertion sheath inverted back over the everting ball on the end of the esophageal tube and into the tab attachment means of the guide collar.

FIG. 13 is the same cross-sectional top view as FIG. 12 except that tab elements 81 and first sheath end 41 have been folded back over everting ball 131 and further, the tab elements 81 have been drawn over ring 74, the partially threaded shaft 76 and cut-outs of threaded shaft 77 where nut 78 can be screwed forward to hold tab elements 81 tightly against threaded shaft 76 and ring 74.

In FIGS. 12 and 13 first sheath end 41 has tab elements 81 constructed and arranged to fold over the tube exterior wall 27 as the first sheath section 45 is in a position inside the tube 15. Preferred tab elements project from the first sheath end 41 and have gripping surfaces, such as, by way of example, without limitation, knurling, holes or loops, slots, buttons and the like, to allow a user to grasp the sheath 19 as the tube 15 is pushed into the esophagus of an animal.

Perspective views shown in FIG. 14A, FIG. 14B and FIG. 14C illustrate the process through which insertion sheath 19 is inverted, moving the first sheath section 45 from position one into position two.

The tab elements 81 are maintained in stationary position at tab attachment means 72 in FIGS. 14A, 14B and 14C. FIG. 14A shows the starting position of insertion sheath 19 as tab elements 81 and first sheath end 41 are inverted over everting ball 131. The tab elements 81 and first sheath end 41 will remain in a stationary position attached to the tab attachment means 72 of guide collar 17 as the everting ball 131 on the first tube end 31 of esophageal tube 15 is thrust outward from guide collar 17. As first sheath section 45 is being inverted over the first tube end 31, the second sheath section 47 is being drawn into tube passageway 25 of second tube end 33. Thus, a fluid conduit is formed in the first sheath surface 51 at the second section 47 for dispensing fluids with the first sheath section 45 of the sheath shielding the exterior surface 27 of the esophageal tube 15 from contact with the oral cavity or esophagus of the animal 13.

Thus, sheath 19 is placed in the esophagus, assuming the second position as the esophageal tube 15 is compelled further into the oral cavity, everting the insertion sheath 19 as it moves down the esophagus, such that the animal does not experience trauma from the abrasion from the esophageal tube 15 or the sheath 19 itself. In position two the insertion sheath 19 can receive fluids or vent gases and can be withdrawn from the esophagus without the animal ever experiencing direct contact with the esophageal tube 15 and without any portion of the sheath 19 placed in direct contact with the oral cavity being compelled lower in the digestive system. Exterior tube surface 27 and second sheath surface 53, which potentially could be unclean or contaminated, a problem in animal husbandry, are never placed in direct contact with the animal's oral cavity or esophagus. The insertion sheath 19 and the esophageal tube 15 are preferably withdrawn from the esophagus and oral cavity in the reverse of the manner in which the insertion sheath 19 and esophageal tube 15 are originally placed. That is, the insertion sheath 19 is withdrawn into tube passageway 25 of esophageal tube 15 as the esophageal tube 15 is withdrawn from the esophagus and oral cavity.

FIG. 14C shows first sheath section 45 totally inverted over esophageal tube 15 and most of second sheath section 47 drawn into passageway 25 of the esophageal tube 15. FIGS. 14A, 14B and 14C depict that the entire first sheath surface 51 comes into contact with a mucosal surface of animal 13 and does not slide along or otherwise abrade the mucosal surface in any manner. This feature has the further benefit of not moving bacteria or other microbes from one location in the oral cavity or esophagus to another location. Each portion of first sheath surface 51 remains in a stationary position once it is everted and assumes the second position. First sheath surface 51 is not contaminated with any environmental pathogens that can be introduced into an animal through contaminated equipment or from poor sanitation practices such as not washing one's hands adequately. No contact is made with first sheath surface 51 once it is attached to the tab attachment means 72. As it is inserted into the oral cavity and esophagus of an animal, a clean first sheath surface 51 is all that ever touches an internal body surface of animal 13.

First sheath surface 51 can be coated with a medicament to cause the esophageal groove to close in an animal. A preferred medicament is selected from the group comprising guanidine, sodium chloride, copper sulfate and sodium bicarbonate solutions. A preferred medicament on first sheath surface 51 contacts the mucosal surface of an animal's oral cavity or esophagus as insertion sheath 19 moves from position one to position two.

Figure 15:
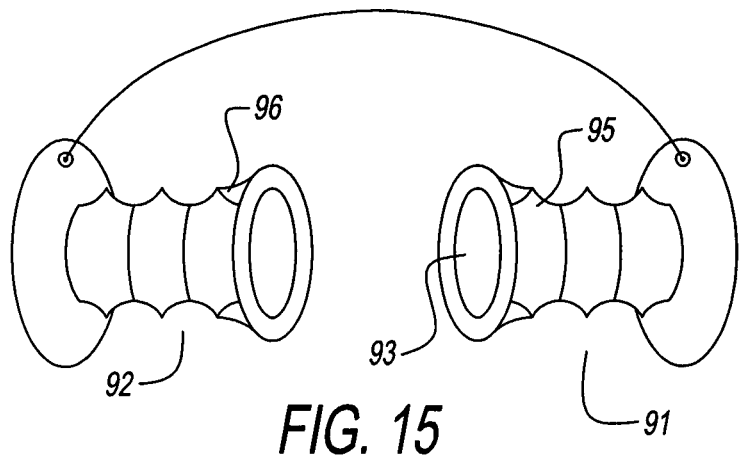
FIG. 15 is a perspective view of interlocking connectors to attach a storage reservoir to the insertion sheath.

Turning now to FIG. 15, a means is shown whereby insertion sheath 19 can be connected to an independent fluid storage reservoir. Small connector 91 has a smaller diameter than large connector 92, allowing it to be screwed into large connector 92. Small connector 91 has a small connector passageway 93 through which the second sheath end 43 can be passed and everted back over the small connector outside wall 95, as shown in FIG. 18.

Figure 16:
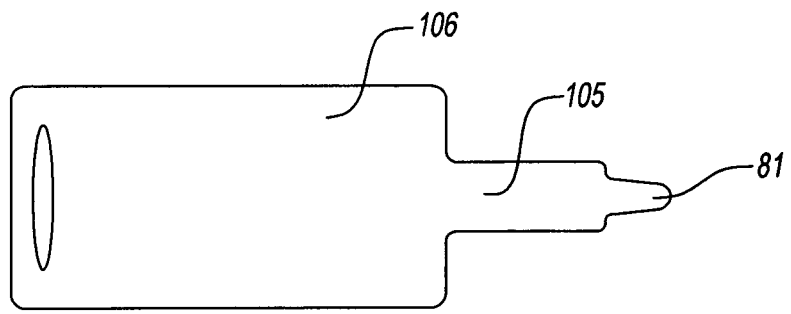
FIG. 16 is a perspective view of the outlet sheath of the storage reservoir with rabbit ear-type tabs to invert it over the connector.
Figure 17:
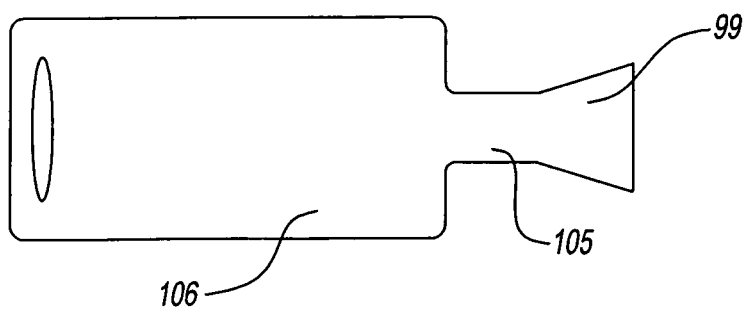
FIG. 17 is a perspective view of the outlet sheath of the storage reservoir with an expanding circumference configuration to invert back over one connector before it engages the other connector that is covered by the insertion sheath.

FIG. 16 is a perspective view of outlet sheath 105 attached to fluid storage reservoir 106. Outlet sheath 105 has tab elements 81 identical to the tab elements 81 of the insertion sheath 19, allowing outlet sheath 105 to be drawn back over the large connector outside wall 96. In like fashion, FIG. 17 shows an outlet sheath 105 with an expanding circumference configuration 99 that can easily be drawn back over large connector outside wall 96.

Figure 18:
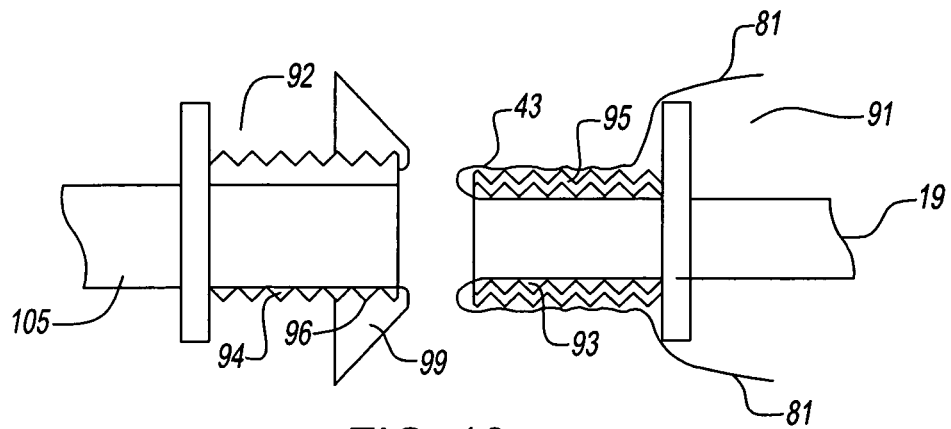
FIG. 18 is a cross sectional top view of the outlet sheath of the storage reservoir attached to the insertion sheath by means of the interlocking connectors.

FIG. 18 is a cross sectional top view of insertion sheath 19 ready to be connected to outlet sheath 105 with an expanding circumference configuration 99. Second sheath end 43 of insertion sheath 19 passes through small connector passageway 93 and is everted back over small connector outside wall 95. Outlet sheath 105 with expanding circumference configuration 99 is passed through large connector passageway 94 and everted back over large connector outside wall 96. As small connector 91 is screwed into large connector 92, a leak proof fluid conduit is formed between insertion sheath 19 and outlet sheath 105.

Figure 19:
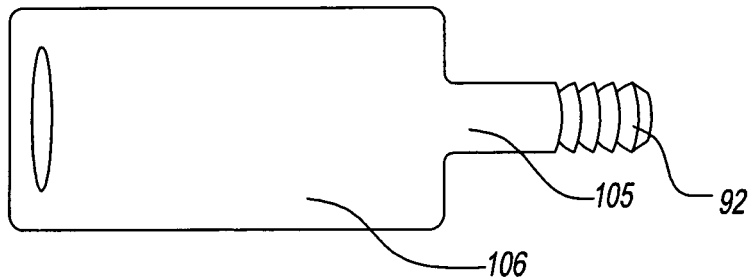
FIG. 19 is a perspective view of a storage reservoir with a permanently attached large connector.

FIG. 19 is a perspective view of a fluid storage reservoir 106 with a large connector 92 attached to outlet sheath 105. Small connector 91 can be screwed into attached large connector 92 of this configuration. The fluid storage reservoir 106 and large connector 92 in FIG. 19 can be washed repeated to provide for multiple uses.

Figure 20:
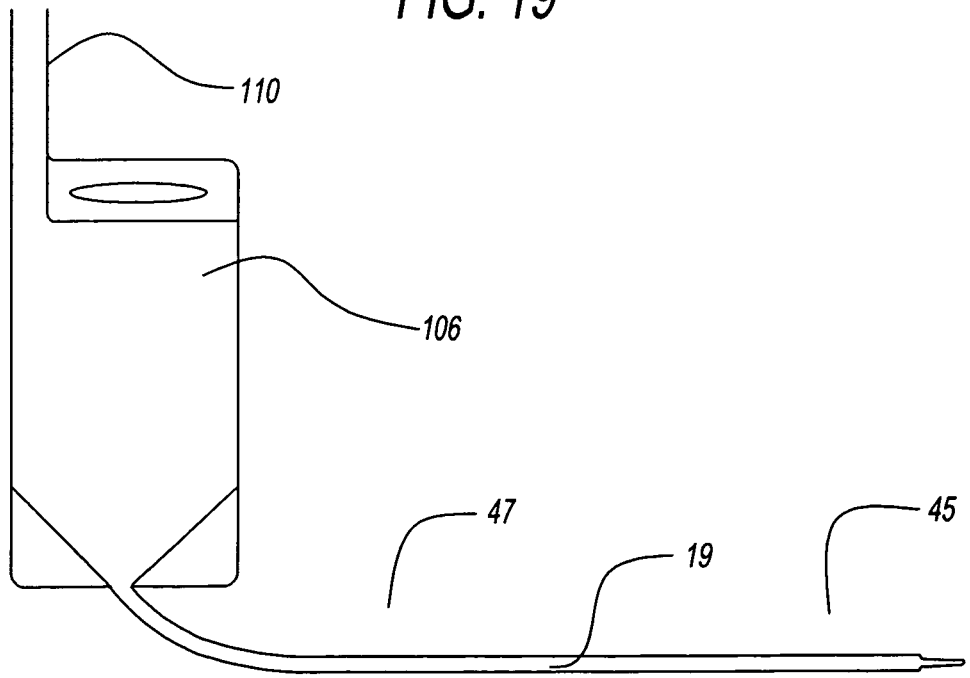
FIG. 20 is a perspective view of an insertion sheath integrally connected to a fluid storage reservoir.

FIG. 20 is a perspective view of insertion sheath 19 integrally attached to fluid storage reservoir 106. Second sheath section 47 is placed in communication with a fluid supply where fluids are to be administered to the animal, or, the sheath 19 further comprises a fluid supply. As depicted, sheath 19 has a third section, fluid storage reservoir 106 integral with the second section 47. The first section 45 and the second section 47 have a volume per unit of length and the third section, fluid storage reservoir 106 has a volume per unit of length greater than either the first section 45 and the second section 47. That is, the third section, fluid storage reservoir 106 expands or is capable of expanding to allow it to hold fluid. Preferably, the sheath has a supply seal [not shown] interposed between the third and second sections. The supply seal can be broken to release fluid from the third section, fluid storage reservoir 106 and into the second section 47 to be administered to the animal.

Preferably, the sheath 19 has a fourth section 110 in communication and integral with the third section, fluid storage reservoir 106. The fourth section 110 has a volume per unit approximately that of or smaller than the first section 45 and second section 47. That is, the fourth section 110 is the same or narrower. The fourth section 110 is used to fill the third section, fluid storage reservoir 106. Fourth section 110 is used for closing the sheath 19. Preferably, the fourth section 110 has a length which is sufficient to form a simple knot, or has other closing means such as zip seals, folds, or receives a clamp [not shown].

Interlocking connectors are not required to form a fluid channel between second section 47 and fluid storage reservoir 106 in the configuration shown in FIG. 20. They are integrally connected.

Fluid storage reservoir 106 of FIGS. 16, 17, 19 and 20 contains a fluid at such time as the insertion sheath 19 is inserted into an animal 13. However, fluid storage reservoir 106 can initially contain a powder to which a fluid is added to form a solution just prior to administration to an animal. As such, the fluid storage reservoir 106 can initially contain a powder or a fluid.

A preferred fluid for dispensing is selected from the group consisting of colostrum, milk, electrolyte solution, oral drugs, vitamins, anti-bloat compounds, amino acids, mineral oil, dissolved or suspended therapeutic powders and granules and nutrients.

The operation of the device 11 of the present invention is presented as a method of administering a fluid to or venting gas from an animal 13. The method comprises the step of administering fluid or venting gas through esophageal tube 15. The esophageal tube 15 has at least one tube wall 21 having an interior tube surface 23 defining a tube passageway 25 and at least one exterior tube surface 27. The at least one tube wall 21 has a tube length to distend from the oral cavity into the esophagus. The exterior tube surface 27 has a diameter not greater than the diameter of the animal's esophagus. The at least one tube wall 21 defines a first tube end 31 and a second tube end 33. The first tube end 31 is for placing in the oral cavity and into the esophagus; with the second tube end 33 extending out of the oral cavity for administering fluids. The method further comprises the step of fitting an insertion sheath 19 to the esophageal tube 15. The insertion sheath 19 has a first sheath end 41, a second sheath end 43, a first sheath section 45 and a second sheath section 47. The first sheath end 41 is at one terminus and a second sheath end 43 is at a second terminus. The insertion sheath 19 is sized and shaped to have the first sheath section 45 towards the first sheath end 41 and the second sheath section 47 toward the second sheath end 43. The insertion sheath 19 has at least one first sheath wall 39 having a length greater than the length of esophageal tube 15 such that upon being extended the sheath 19 forms a cylinder-like form. The first sheath wall 39 is flexible and has at least one first sheath surface 51 and at least one second sheath surface 53. Insertion sheath 19 has a first position in which the first sheath surface 51 of the first sheath section 45 is positioned facing itself and the second sheath surface 53 is facing away from itself and a second position in which the second sheath surface 53 of the first sheath section 45 faces itself and the first sheath surface 51 faces away from itself. The method further comprises the step of moving the insertion sheath 19 from the first position to the second position upon pulling the insertion sheath 19 through esophageal tube 15 and folding the first sheath section 45 at the first tube end 31 of esophageal tube 15 to evert the first sheath section 45 and draw the second sheath section 47 of insertion sheath 19 into the tube passageway 25. A fluid conduit for dispensing fluids is formed by the second sheath section 47 with the first sheath section 45 of the sheath 19 shielding the exterior surface 27 of esophageal tube 15 from contact with the oral cavity or esophagus of the animal 13.

The step of moving the sheath from the first position to the second position is preferably performed as esophageal tube 15 is moved down and through the oral cavity of an animal and into the esophagus.

Thus, preferred methods and devices of the present invention have been described with the understanding that such methods and devices are capable of modification and alteration without departing from the teaching herein. Therefore, the present invention should not be limited to the precise details set forth but should encompass the subject matter of the claims which follow, and their equivalents.

I claim:

1. A device for administering a fluid to an animal, said animal having an oral cavity, esophagus and stomach, said fluid administered through a tube and said tube having at least one tube wall having an interior tube surface defining a tube passage and at least one exterior tube surface, said at least one tube wall having a tube length to distend from the oral cavity into the esophagus, said exterior tube surface having a diameter not greater than the diameter of the animal's esophagus, said at least one tube wall defining a first tube end and a second tube end, said first tube end for placing in said oral cavity and into said esophagus and said second tube end for extending out of said oral cavity for administering fluids; said device comprising:

a sheath having a first sheath section and a second sheath section, said sheath sized and shaped to have said first sheath section towards a first sheath end and said second sheath section toward a second sheath end, said sheath having a length and width having a expanded width configuration and a folded width configuration, said length greater than the length of said tube such that upon being extended said sheath forms a cylinder, said expanded width configuration allowing said sheath to be pulled over said exterior surface of said tube, and said folded width configuration comprising one or more folds along said length to allow the sheath to pass through the tube passage, said sheath having at least one first sheath wall, said at least one sheath wall being flexible and having at least one first sheath surface and at least one second sheath surface, said sheath having a first position in which said first sheath surface of said first sheath section is positioned facing itself and said second sheath surface is facing away from itself with the width in said folded width configuration and a second position in which said second sheath surface of said first sheath section faces itself and said first sheath surface faces away from itself with the width in said expanded width configuration, said sheath moving from said first position to said second position upon folding said first sheath section at said first sheath end over said tube to invert said first sheath section of said sheath and to draw said second sheath section of said sheath into the tube passageway, forming a fluid conduit for dispensing fluids with said first sheath section of said sheath shielding said exterior surface of tube from contact with the oral cavity or esophagus of an animal, said sheath prior to assuming said second position maintained in with said first position.

2. The device of claim 1 wherein said first sheath end has tab elements constructed and arranged to fold over the tube exterior wall as said sheath is in a position inside said tube.

3. The device of claim 2 wherein said tab elements have gripping surfaces to allow a user to grasp as said tube is pushed into the esophagus of an animal.

4. The device of claim 3 wherein said tab elements cooperate with a ring to permit a tight grip on said sheath, said ring for assuming a position in sliding engagement with said tube.

5. The device of claim 3 wherein said sheath has a third section integral with said second section, said first section and said second section having a volume per unit of length and said third section having a volume per unit of length in which said third section has a volume per unit of length greater than said first section and said second section to allow said third section to hold fluid.

6. The device of claim 5 wherein said sheath has a fourth section in communication and integral with said third section, said fourth section having a volume per unit approximately that of said first section and second section, said fourth section having said second end for filling said sheath and storing fluid in said third section.

7. The device of claim 6 wherein said fourth section further comprising closing means.

8. The device of claim 7 wherein said closing means comprise a fourth section having a length capable of forming a knot.

9. The device of claim 7 wherein said closing means comprise a clamp.

10. The device of claim 2 further comprising coating of said first sheath surface of said first sheath section with a chemical.

11. The device of claim 10 wherein said chemical used to coat said first sheath surface is selected from the group comprising guanidine, sodium chloride copper sulphate and sodium bicarbonate solutions.

12. The device of claim 1 wherein said second sheath section is in communication with a fluid supply.

13. The device of claim 1 further comprising a fluid supply.

14. The device of claim 13 wherein said fluid is selected from the group consisting of colostrum, milk, electrolyte solution, oral drugs, vitamins, anti-bloat compounds, amino acids, mineral oil, dissolved or suspended therapeutic powders and granules and nutrients.

15. The device of claim 1 further comprising a tube.

16. The device of claim 15 wherein said tube has an everting ball.

17. The device of claim 15 wherein said tube has at least three ridges along said length of said exterior tube surface.

18. The device of claim 15 wherein said tube is comprised of one or more materials selected from the group consisting of metals, plastics and rubber.

19. The device of claim 1 wherein said second sheath section of said sheath is withdrawn from said tube passageway as said tube is withdrawn from the animal.

20. The device of claim 1 wherein said sheath is two times the length of said tube.

21. The device of claim 1 wherein said sheath is comprised of one or more materials selected from the group consisting of metals, polyfoils, or plastic.

22. The device of claim 1 further comprising a ring attached to said sheath at said first sheath end to maintain a stationary position and prevent said first sheath end from being pushed into said oral cavity upon placement in the animal.

23. The device of claim 1 wherein said sheath stored as a roll and unwinds as an individual sheath is pulled for use.

24. The device of claim 1 wherein said sheath is stored folded in an enclosure and presents tab elements for dispensing.

25. The device of claim 1 wherein said at least one sheath wall is corrugated to cooperate with an everting ball of a tube.

26. A method of providing a fluid to or venting gas from an animal comprising the step of providing a device as set forth in claim 1 and inserting said tube as said sheath moves from said first position to said second position and venting or providing fluid through said sheath in said second position.

27. The device of claim 1 wherein said one or more folds of said width are accordion-like.

28. The device of claim 1 wherein said expanded width is up to approximately 1 ⅜ inches and said folded width is down to ⁷⁄₁₆ inch or less.

\* \* \* \* \*